US012765787B2

(12) United States Patent
Shimuta

(10) Patent No.: US 12,765,787 B2
(45) **Date of Patent: *Oct. 20, 2026**

(54) METHOD OF ESTIMATING PERIPHERAL BLOOD PRESSURE AND BIOLOGICAL DATA MEASUREMENT SYSTEM

(71) Applicant: Murata Manufacturing Co., Ltd., Nagaokakyo (JP)

(72) Inventor: Toru Shimuta, Nagaokakyo (JP)

(73) Assignee: MURATA MANUFACTURING CO., LTD., Nagaokakyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 18/817,570

(22) Filed: Aug. 28, 2024

(65) Prior Publication Data

US 2024/0415398 A1 Dec. 19, 2024

Related U.S. Application Data

(63) Continuation of application No. PCT/JP2023/009623, filed on Mar. 13, 2023.

(30) Foreign Application Priority Data

Mar. 31, 2022 (JP) ................................ 2022-061021
Aug. 12, 2022 (JP) ................................ 2022-128969

(51) Int. Cl.
*A61B 5/021* (2006.01)
*A61B 5/00* (2006.01)
*A61B 5/024* (2006.01)

(52) U.S. Cl.
CPC ........ *A61B 5/02125* (2013.01); *A61B 5/6826* (2013.01); *A61B 5/02416* (2013.01)

(58) Field of Classification Search
None
See application file for complete search history.

(56) References Cited

U.S. PATENT DOCUMENTS 10,624,586 B2 4/2020 Noguchi et al.
10,813,561 B2 10/2020 Kwon et al.
(Continued)

FOREIGN PATENT DOCUMENTS

JP H1189806 A * 4/1999
JP 2001-137203 A 5/2001
(Continued)

OTHER PUBLICATIONS

Elgendi et al., "The use of photoplethysmography for assessing hypertension". npj Digital Medicine 2:60 (2019) (Year: 2019).*
(Continued)

*Primary Examiner* — Yi-Shan Yang
(74) *Attorney, Agent, or Firm* — ArentFox Schiff LLP

(57) ABSTRACT

A method of estimating a peripheral blood pressure and a biological data measurement system are provided by which the magnitude of a blood pressure in a capillary or an arteriole at a periphery may be estimated in a simple and non-invasive manner. Acquiring a photoplethysmographic signal from a capillary or an arteriole at a periphery of a user who is a subject by using a photoplethysmographic sensor; and calculating a peripheral blood pressure index based on the steepness of the rising edge of the photoplethysmographic signal are performed at the biological data measurement system, the peripheral blood pressure index serving as an index of the magnitude of a blood pressure in the capillary or the arteriole at the periphery. The magnitude of the blood pressure in the capillary or the arteriole at the periphery is estimated based on the peripheral blood pressure index.

17 Claims, 11 Drawing Sheets

(56) References Cited

U.S. PATENT DOCUMENTS

| | | | | |
|---|---|---|---|---|
| 11,786,136 | B2 | 10/2023 | Igami | |
| 2016/0302735 | A1 | 10/2016 | Noguchi et al. | |
| 2018/0177413 | A1 | 6/2018 | Kwon et al. | |
| 2019/0053768 | A1* | 2/2019 | Enari | A61B 5/02108 |
| 2020/0155018 | A1* | 5/2020 | Igami | A61B 5/02444 |

FOREIGN PATENT DOCUMENTS

| | | | |
|---|---|---|---|
| JP | 2018-102906 | A | 7/2018 |
| JP | 2019-208617 | A | 12/2019 |
| WO | 2015/098977 | A1 | 7/2015 |
| WO | 2019/003549 | A1 | 1/2019 |

OTHER PUBLICATIONS

International Search Report received for PCT Patent Application No. PCT/JP2023/009623, mailed on May 9, 2023, 2 pages (English Translation Only).

* cited by examiner

METHOD OF ESTIMATING PERIPHERAL BLOOD PRESSURE AND BIOLOGICAL DATA MEASUREMENT SYSTEM

CROSS REFERENCE TO RELATED APPLICATIONS

This application is a continuation of International Application No. PCT/JP2023/009623, filed Mar. 13, 2023, which claims priority to Japanese Patent Application No. 2022-061021, filed Mar. 31, 2022, and Japanese Patent Application No. 2022-128969, filed Aug. 12, 2022, the entire contents of each of which are hereby incorporated in their entirety.

TECHNICAL FIELD

The present disclosure is directed to a method of estimating a peripheral blood pressure and a biological data measurement system by which a blood pressure in a capillary or an arteriole at a periphery of a subject (user) is estimated.

BACKGROUND

A plethysmographic wave propagating in an artery of a user is used as an index used to estimate the health condition of the user. A plethysmographic waveform changes in response to a change in the blood pressure of a user at a measurement position. International Publication No. 2015/098977 (the "'977 Publication"), the entire contents of which is hereby incorporated in its entirety, discloses a plethysmographic waveform measuring apparatus to measure a blood pressure without causing a heavy burden on a human body. The plethysmographic waveform measuring apparatus according to the '977 Publication is configured to estimate blood pressure data of a human body based on temporal information regarding the rate of cardiac beat and the plethysmographic waveform of the human body.

However, the plethysmographic waveform measuring apparatus according to the '977 Publication is configured to estimate blood pressure data in an artery and is not configured to estimate blood pressure data in a capillary or an arteriole at a periphery of a user.

SUMMARY

Accordingly, it is an object of the present disclosure to provide a method of estimating a peripheral blood pressure and a biological data measurement system by which such peripheral blood pressure data may be estimated in a non-invasive manner.

In an exemplary aspect, the present disclosure provides a method of estimating a peripheral blood pressure including acquiring a photoplethysmographic signal from a capillary or an arteriole at a periphery of a subject by using a photoplethysmographic sensor; calculating a peripheral blood pressure index based on steepness of a rising edge of the photoplethysmographic signal, the peripheral blood pressure index serving as an index of a magnitude of a blood pressure in the capillary or the arteriole at the periphery; and estimating the magnitude of the blood pressure in the capillary or the arteriole at the periphery based on the peripheral blood pressure index, and the acquiring and the calculating are performed at a biological data measurement system.

The present disclosure also provides a biological data measurement system including a sensing device including a photoplethysmographic sensor configured to acquire a photoplethysmographic signal from a capillary or an arteriole at a periphery of a subject; and a computer including a signal processing device configured to calculate a peripheral blood pressure index based on steepness of a rising edge of the photoplethysmographic signal, the peripheral blood pressure index serving as an index of a magnitude of a blood pressure in the capillary or the arteriole at the periphery.

According to the present disclosure, a photoplethysmographic signal from a capillary or an arteriole at a subject's periphery is acquired by using a photoplethysmographic sensor, and a peripheral blood pressure index, which serves as an index of a magnitude of a blood pressure in the capillary or the arteriole at the subject's periphery, is calculated based on the steepness of the rising edge of the acquired photoplethysmographic signal. The magnitude of the blood pressure in the capillary or the arteriole at the subject's periphery is estimated based on the calculated peripheral blood pressure index.

Accordingly, the present disclosure may provide a method of estimating a peripheral blood pressure and a biological data measurement system by which the magnitude of a blood pressure in a capillary or an arteriole at a periphery may be estimated in a simple and non-invasive manner without causing a burden on a subject.

BRIEF DESCRIPTION OF DRAWINGS

In the descriptions that follow, like parts are marked throughout the specification and drawings with the same numerals, respectively. The drawings are not necessarily drawn to scale and certain drawings may be shown in exaggerated or generalized form in the interest of clarity and conciseness. The disclosure itself, however, as well as a mode of use, further features and advances thereof, will be understood by reference to the following detailed description of illustrative implementations of the disclosure when read in conjunction with reference to the accompanying drawings, wherein.

DETAILED DESCRIPTION

Figure 1:
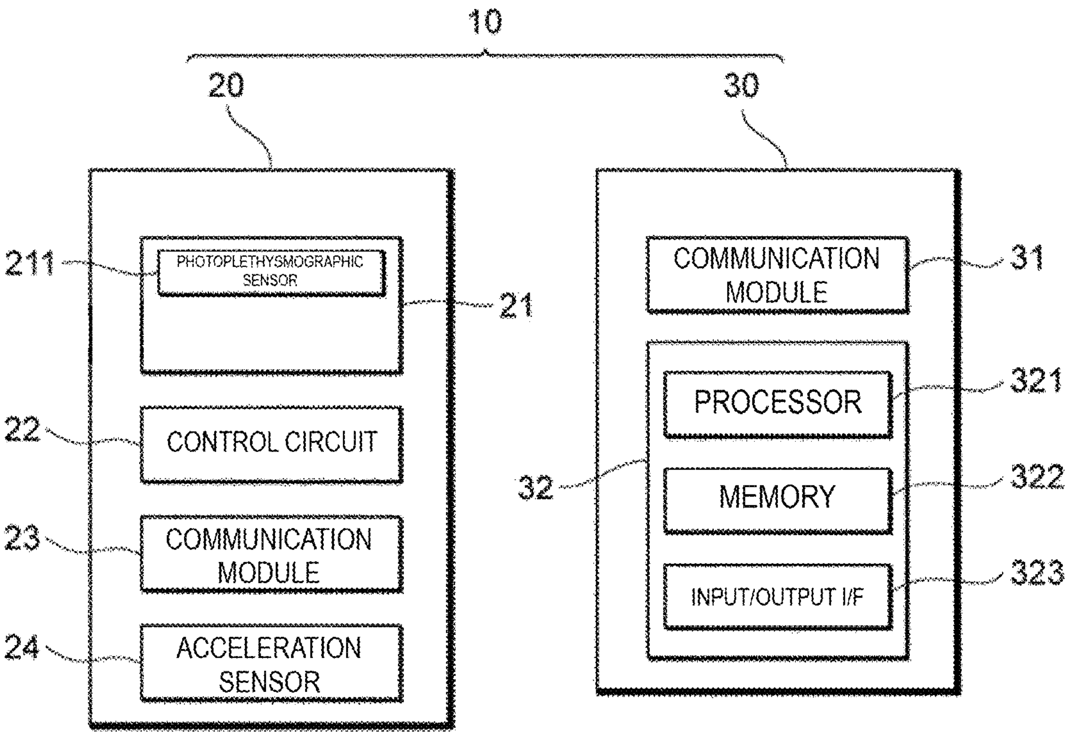
FIG. 1 is an illustration depicting a configuration of a biological data measurement system in accordance with aspects of the present disclosure.

Hereinbelow, aspects of the present disclosure will be described. In a following description of the drawings, the same or similar components will be represented with use of the same or similar reference characters. The drawings are exemplary, sizes or shapes of portions are schematic, and technical scope of the present disclosure should not be understood with limitation to the aspects.

Hereinafter, an aspect of the present disclosure will be described with reference to the drawings. The same reference symbols denote the same or similar elements, and duplicate description will be omitted.

FIG. 1 is an illustration depicting a configuration of a biological data measurement system 10 according to an aspect of the present disclosure. The biological data measurement system 10 includes a sensing device 20 configured to measure biological data of a user who is a subject and a computer 30 configured to be able to communicate with the sensing device 20.

According to exemplary aspects, the sensing device 20 can include a wearable device having a structure attachable to a peripheral part (for example, a finger) of the user. The sensing device 20 includes a biological sensor 21 configured to obtain biological data from a peripheral part (for example, a finger) of the user, a control circuit 22 configured to control operation of the biological sensor 21, a communication module 23 configured to transmit a measurement result obtained by using the sensing device 20 to the computer 30 via a wireless network or a wireline network, and an acceleration sensor 24 configured to measure the acceleration during a movement of the sensing device 20.

The biological sensor 21 includes, for example, a photoplethysmographic sensor 211 configured to measure an index value representing a peripheral blood pressure of the user. A peripheral blood pressure is defined as a blood pressure in a capillary or an arteriole at a periphery in the present disclosure. An index representing a blood pressure in an arteriole or a capillary, especially in a capillary, is referred to as a peripheral blood pressure index in the present disclosure. An arteriole is a thin artery having a diameter of, for example, approximately 20 to 200 μm and is a blood vessel located between an artery and a capillary. A capillary is a thin blood vessel having a diameter of, for example, approximately 10 μm and connects an artery and a vein.

Although the term "peripheral blood pressure" is sometimes used to refer to a blood pressure at a wrist or a blood pressure at an ankle measured by using a cuff-type blood pressure monitor, the peripheral blood pressure in such usage indicates a value measured at a thick artery (such as the radial artery) and differs from a blood pressure in an arteriole or a capillary in the present disclosure. The blood pressure in a thick artery is a blood pressure usually measured by using a cuff-type blood pressure monitor, and a blood pressure in a blood vessel decreases as blood moves from an artery to an arteriole and further to a capillary. The degree of such a decrease in blood pressure depends on, for example, a measurement site, the state of a person's blood vessel (such as arteriosclerosis), a mental condition (such as the state of autonomic nerves), an environment (such as air temperature and noise), and clothes.

The peripheral blood pressure index is expected to have the following two features (1) and (2). (1) For a healthy blood vessel, the peripheral blood pressure index is substantially proportional to the blood pressures (at an upper arm and a wrist) under the condition that a blood vessel resistance is invariant. (2) Contracting a blood vessel by cooling a region near a measurement site decreases the peripheral blood pressure index. Contracting a blood vessel means increasing the blood vessel resistance at a periphery, which sometimes leads to an increase in the blood pressures at an upper arm and a wrist.

Thus, according to an exemplary aspect, the photoplethysmographic sensor 211 can be equipped with three LEDs as a light source and is configured to measure a photoplethysmographic signal at three wavelengths (green, red, and near-infrared). Since oxyhemoglobin is present in the blood in an artery and has characteristics of absorbing incident light, a photoplethysmographic signal can be measured by sensing as a function of time the amount of blood flow that varies (the blood vessel volume that varies) according to cardiac pulsation. A red LED is mounted to derive oxygen saturation and is not indispensable for extracting the peripheral blood pressure index. The photoplethysmographic sensor 211 is equipped with a photodiode (PD) as a photosensitive element. The photoplethysmographic sensor 211 is configured to cause the three LEDs to sequentially emit light in a time-sharing mode, and the PD is configured to receive reflected or scattered light that returns from the skin of a finger irradiated with the light from the LEDs.

The communication module 23 is configured to transmit a measurement result obtained by using the sensing device 20 (for example, a photoplethysmographic signal measured by the photoplethysmographic sensor 211 and the acceleration of the sensing device 20 measured by the acceleration sensor 24) to the computer 30 via the wireless network or the wireline network.

The acceleration sensor 24 is configured to measure the acceleration during a movement of the sensing device 20 while the user changes the posture to measure a photoplethysmographic signal. The acceleration sensor 24 is a triaxial acceleration sensor configured to detect a direction in which gravitational acceleration is exerted, and the detected signal is used to estimate the height at which the sensing device 20 is attached to the user, deduce the position at which the sensing device 20 is attached to the user (for example, the position of the 'heart of a user), and deduce the 'posture of a user, for example, standing (standing position), sitting (sitting position), or lying flat on the back (supine position).

Examples of the computer 30 include a multi-functional mobile phone called a smartphone and a general-purpose computer (for example, a notebook personal computer, a desktop personal computer, a tablet terminal, and a server computer). The computer 30 includes a communication module 31 and a signal processing device 32; the communication module 31 is configured to receive from the sensing device 20 via the wireless network or the wireline network a measurement result obtained by using the biological sensor 21; the signal processing device 32 is configured to perform a process of deducing the 'biological data of a user from the measurement result obtained by using the biological sensor 21. The signal processing device 32 includes a processor 321, a memory 322, and an input/output interface 323.

A green LED and a near-infrared LED are used to measure respective photoplethysmographic waveforms (e.g., volume plethysmographic waveforms), and the signal processing device 32 is configured to compute a first derivative (e.g., velocity plethysmographic waveform) and a second derivative (e.g., acceleration plethysmographic waveform) of each of the two photoplethysmographic waveforms; the signal processing device 32 is configured to derive plethysmographic-waveform feature values from each cardiac cycle of the first derivative and the second derivative. Subsequently, the peripheral blood pressure index is calculated based on the plethysmographic-waveform feature values. In addition, the signal processing device 32 is configured to, based on the signal from the acceleration sensor 24, estimate the height of the site at which the sensing device 20 is attached to the user and deduce the' posture of a user.

Figure 2:
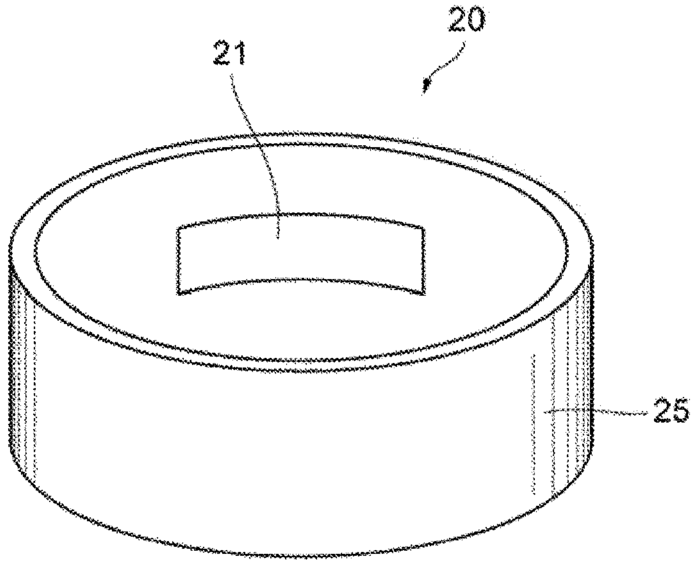
FIG. 2 is an illustration depicting an external appearance of a sensing device in accordance with aspects of the present disclosure.

FIG. 2 is an illustration depicting an external appearance of the sensing device 20 according to an aspect of the present disclosure. Examples of a measurement site for a photoplethysmographic waveform include a wrist, a neck, a face, and an ear, but a finger is a preferable measurement site. The reason for the preference is that a photoplethysmographic waveform is easily measured because a finger has a relatively thin epidermal region and that feature values are readily stabilized because capillary paths are not as complicated as those in the face or other parts. A ring-type wearable device that includes an optical sensor and that is configured to be worn on a finger is preferable as a device for measuring a photoplethysmographic waveform. This is because a ring-type wearable device is unlikely to cause great discomfort or displeasure if being worn for a long time during a continuous or intermittent measurement. However, this example is not meant to be limiting, and a wrist-band type device to be attached to a wrist, a wrist-watch type device, an earphone type device to be attached to an ear, a patch type device to be attached to a skin, or a neck-band type device to be put around a neck may be adopted as a wearable device. Further, the device need not be wearable and may be a portable device, such as a smartphone, or an immobile device configured to perform measurement on a finger in contact with a sensor.

Moreover, the sensing device 20 can include a ring-like casing 25 configured to be attachable to the finger of a user in an aspect of the present disclosure. For example, the casing 25 has a hollow cylindrical form in an example depicted in FIG. 2. The biological sensor 21 is affixed to the inner surface of the casing 25 (inside surface of the hollow cylinder) so as to face the pad of the finger of a user when the sensing device 20 is attached to the finger of a user. The form of the casing 25 is not limited to the hollow cylinder-like form and can be, for example, a cylinder-like form covering the finger of a user from above (for example, as a finger cot) with or without the bottom of the cylinder (the portion that the fingertip touches).

Figure 3:
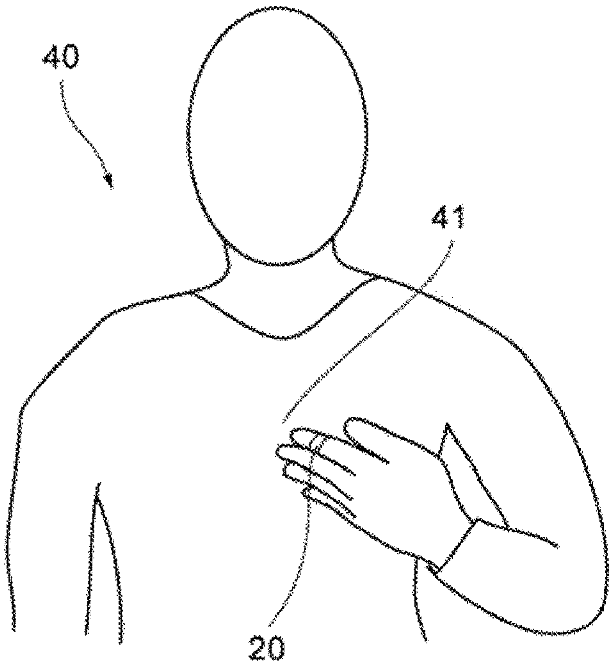
FIG. 3 is an illustration depicting an example of a posture of a user to measure biological data in accordance with aspects of the present disclosure.

FIG. 3 depicts an example of a posture of a user 40 to measure biological data In accordance with an exemplary aspect. In this example, the user 40 keeps the finger to which the sensing device 20 is attached still at the position of a heart 41, and the sensing device 20 obtains biological data from the finger of the user 40. The position (e.g., measurement position) at which the sensing device 20 is located during biological data measurement is not limited to the position of the chest (heart) 41 of the user 40 and can be the position of the face (forehead) or the position of the stomach (navel) of the user 40. The posture of the user 40 during biological data measurement may be a sitting position or a supine position.

Figure 4:
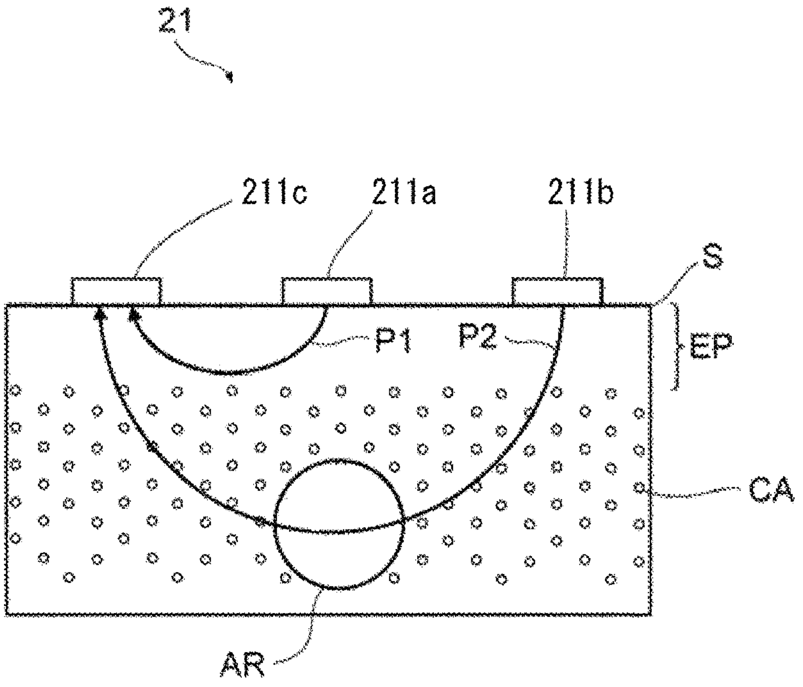
FIG. 4 is an illustration schematically depicting acquisition of a photoplethysmographic signal by using the sensing device in accordance with aspects of the present disclosure.

Referring to FIG. 4, description will be given with regard to the acquisition of a photoplethysmographic signal by using the biological sensor 21. FIG. 4 is a schematic cross-sectional view of the biological sensor 21 closely attached to a body surface S of the user.

The biological sensor 21 includes light emitting elements **211*a* and 211*b* and a photosensitive element 211*c*. The biological sensor 21 is configured to emit light to the body surface S and receive light absorbed or reflected by an epidermal region EP and multiple capillaries CA of the user and an arteriole AR from which each of the capillaries CA branches off. In the present aspect, description will be given with regard to a case where a single photosensitive element 211*c* is disposed for the light emitting elements 211*a* and 211*b* as a light source. Note that, for each of the light emitting elements 211*a* and 211*b***, the corresponding photosensitive element may be disposed.

The light emitting element **211*a* is preferably an LED or a laser having a wavelength of, for example, around blue to yellow green (preferably around 500 to 550 nm) and is a green LED in the present aspect. The light emitting element 211*b* is preferably an LED or a laser having a wavelength of, for example, around red to near-infrared (preferably around 750 to 950 nm) and is a near-infrared LED in the present aspect. The light emitting element 211*a* is configured to emit light in a wavelength range strongly absorbed by living tissue, and the light emitting element 211*b* is configured to emit light in a wavelength range relatively weakly absorbed by living tissue. Description will be given hereinafter on the assumption that the light emitting element 211*a* is a green LED 211*a* and the light emitting element 211*b* is a near-infrared LED 211*b*. A photodiode (PD) or a phototransistor is used as the photosensitive element 211*c***. A Si photodiode is preferred.

The green LED **211*a* is disposed closer to the photosensitive element 211*c* than the near-infrared LED 211*b* is. For example, the distance between the green LED 211*a* and the photosensitive element 211*c* is preferably set to approximately 1 to 3 mm, and the distance between the near-infrared LED 211*b* and the photosensitive element 211*c* is preferably set to approximately 5 to 20 mm. Since the green LED 211*a* is disposed closer to the photosensitive element 211*c* than the near-infrared LED 211*b* is, an optical receive signal generated by the light from the green LED 211*a* is caused to include more information regarding a shallow region of the skin than an optical receive signal generated by the light from the near-infrared LED 211*b*** does.

The light emitted from the green LED **211*a* is absorbed by the epidermal region EP of the user and the capillaries CA located on the epidermal region EP side, and transmitted light or reflected light is detected by the photosensitive element 211*c*. The light emitted from the near-infrared LED 211*b* is absorbed by the epidermal region EP, the capillaries CA, and the arteriole AR located deeper inside the body than the epidermal region EP of the user and is detected by the photosensitive element 211*c*. FIG. 4 schematically depicts the light from the green LED 211*a* as light along an optical path P1 and the light from the near-infrared LED 211***b* as light along an optical path P2.

Plethysmographic-waveform feature values that have the features (1) and (2) described for the peripheral blood pressure index are extracted in the following manner. The sensing device 20 attachable to a finger as depicted in FIG. 2, which is equipped with the photoplethysmographic sensor 211, is prepared, and the user 40 puts a wrist-type cuff blood pressure monitor on the left wrist (or the right wrist) and puts the sensing device 20 on the index finger (or another finger) of the left hand. Then, while sitting still, the user 40 keeps the left hand, to which the sensing device 20 is attached, at stomach (navel) height, at chest height, and at face (forehead) height to measure a photoplethysmographic waveform and a blood pressure. Since the cuff obstructs blood flow in the finger in a simultaneous measurement of the photoplethysmographic waveform and the blood pressure, the blood pressure is measured after the measurement of the photoplethysmographic waveform ends. Next, the left elbow is cooled with a refrigerant while the left hand is kept at chest height. The photoplethysmographic waveform and the blood pressure are measured after the elbow is cooled for a few minutes. Plethysmographic-waveform feature values that have the features (1) and (2) described for the peripheral blood pressure index are derived in the following manner from the photoplethysmographic waveform measured in this way.

Figure 5:
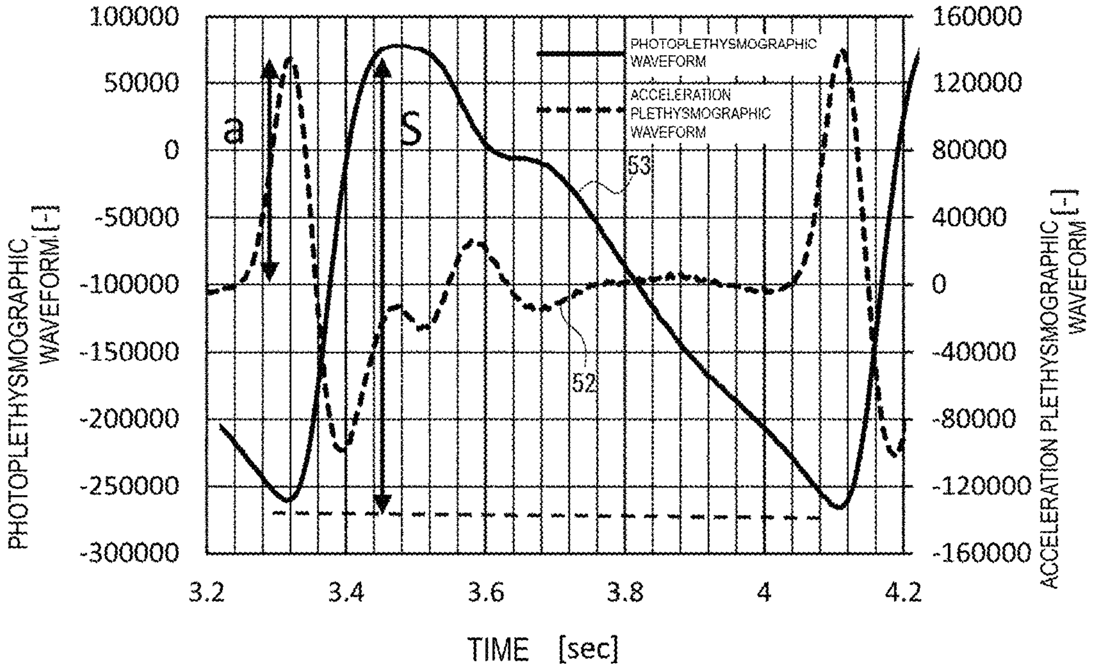
FIG. 5 is a graph describing a maximum amplitude of a photoplethysmographic signal in accordance with aspects of the present disclosure.

The graph in FIG. 5 depicts an acceleration plethysmographic signal 52 that is a second derivative of a photoplethysmographic (volume photoplethysmographic) signal 53. The horizontal axis on the graph represents time [sec], and the vertical axis on the graph represents signal intensities of the acceleration plethysmographic signal 52 and the photoplethysmographic signal 53. As depicted in FIG. 5, the height of the plethysmographic waveform (e.g., maximum amplitude) S of the photoplethysmographic signal 53 is defined as the height of a local maximum after the baseline is corrected so that the slope of a straight line connecting local minima becomes zero.

Figure 6:
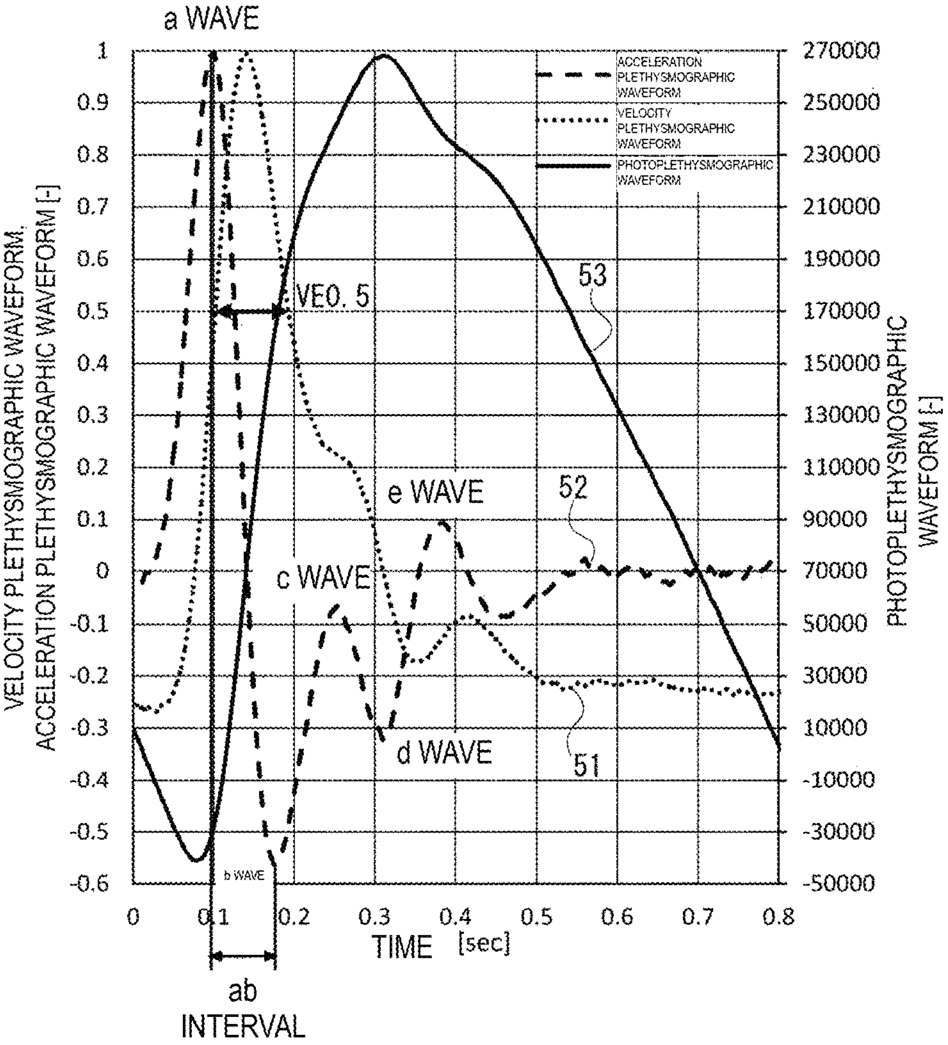
FIG. 6 is a first graph describing each waveform element necessary to calculate plethysmographic-waveform feature values for deriving a peripheral blood pressure index in accordance with aspects of the present disclosure.
Figure 7:
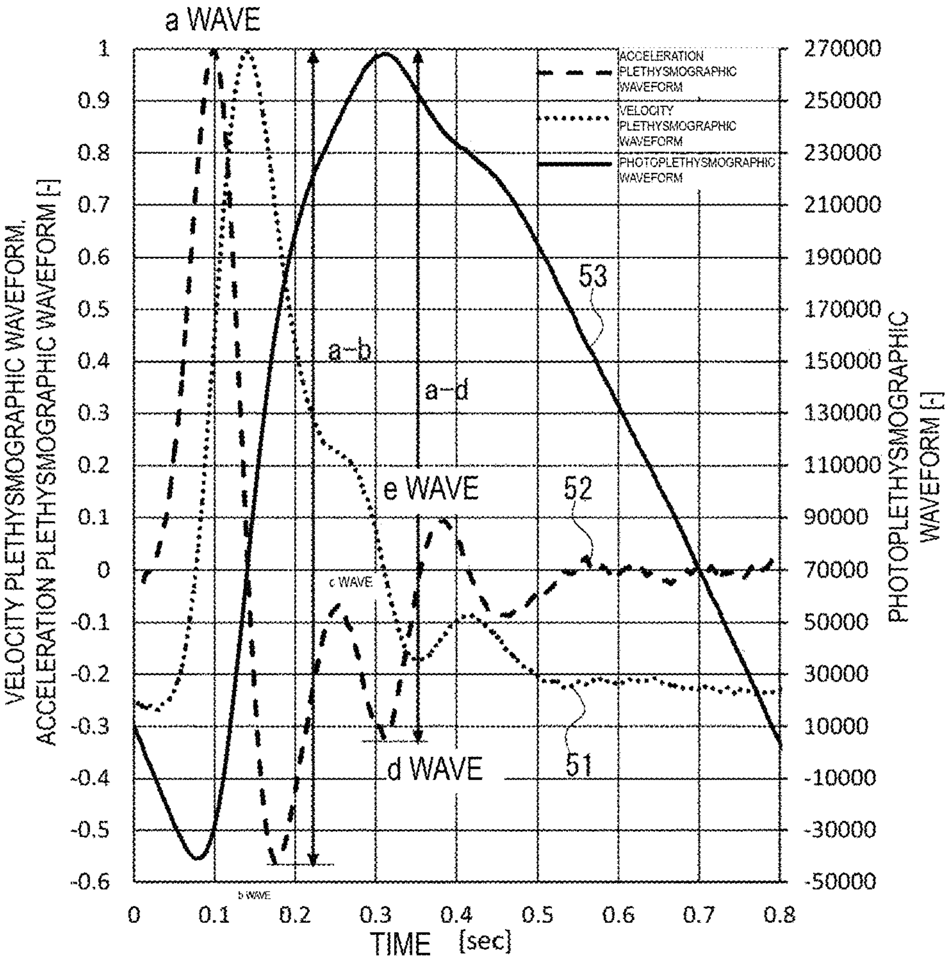
FIG. 7 is a second graph describing each waveform element necessary to calculate plethysmographic-waveform feature values for deriving a peripheral blood pressure index in accordance with aspects of the present disclosure.

As depicted in the graph in FIG. 6, VE0.5 refers to the full width at half maximum of the highest peak of a velocity plethysmographic signal 51 that is a first derivative of the photoplethysmographic signal 53. The horizontal axis on the graph in FIG. 6 represents time [sec], and the vertical axis on the graph represents signal intensities of the velocity plethysmographic signal 51, the acceleration plethysmographic signal 52, and the photoplethysmographic signal 53. The velocity plethysmographic signal 51 and the acceleration plethysmographic signal 52 have been subjected to a normalization process so that the maximum of each signal becomes 1. As depicted in FIG. 6, the acceleration plethysmographic signal 52 has peaks (local maxima and local minima) referred to as the a wave, the b wave, the c wave, the d wave, and the e wave. The a wave, the c wave, and the e wave each have a convex upward waveform, and the b wave and the d wave each have a convex downward waveform. The difference between the peak time of the a wave and the peak time of the b wave is referred to as the ab interval. The signal intensities at the peak of the a wave, the b wave, the c wave, the d wave, and the e wave are referred to as a, b, c, d, and e, respectively. As depicted in the graph in FIG. 7, for the acceleration plethysmographic signal 52, the difference in peak value between the a wave and the b wave is referred to as a−b, and the difference in peak value between the a wave and the d wave is referred to as a−d. The horizontal axis and the vertical axis on the graph in FIG. 7 are the same as those on the graph in FIG. 6.

As described above, the peripheral blood pressure index is characterized by the feature (1) of being substantially proportional to the blood pressures at an upper arm and a wrist, and the following three feature values are extracted as plethysmographic-waveform feature values characterized by the feature (1).

1/VE0.5 a/S (a−b)/(a−d)

Figure 8A:
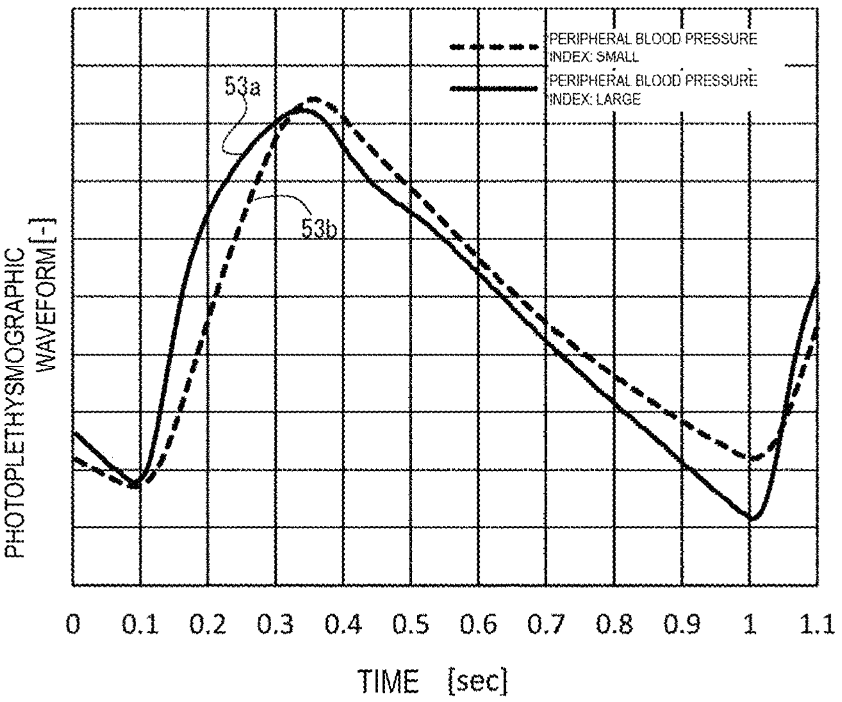
FIGS. 8(*a*) to 8 (*c*) illustrate graphs depicting correlations between the steepness of the rising edge of a photoplethysmographic signal and plethysmographic-waveform feature values in accordance with aspects of the present disclosure.
Figure 8B:
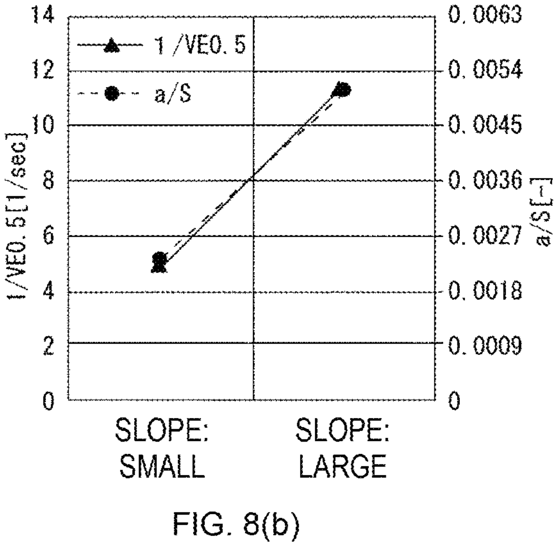
Figure 8C:
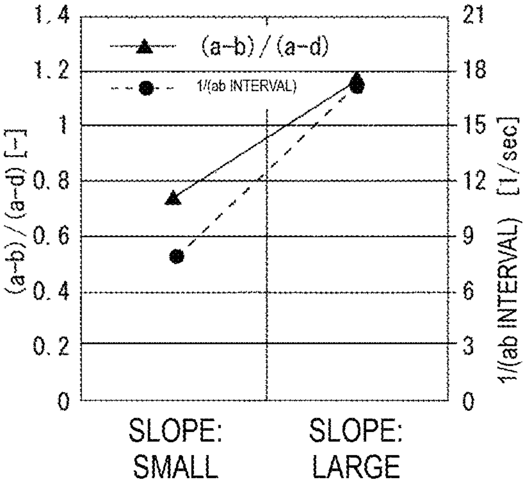
Figure 9A:
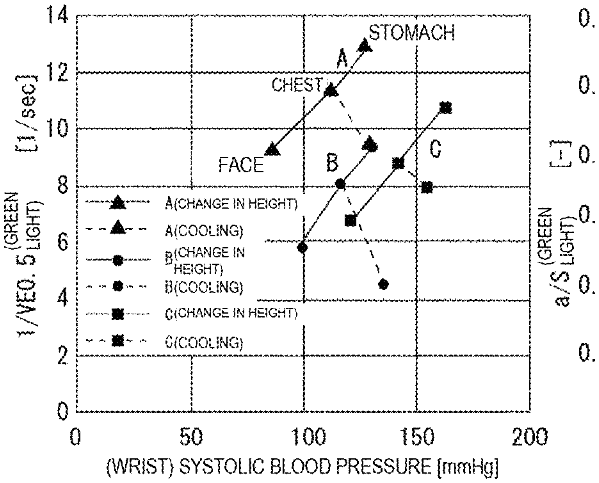
FIGS. 9(*a*) to 9(*d*) illustrate graphs depicting results representing relationships between the systolic blood pressure and plethysmographic-waveform feature values derived from photoplethysmographic signals measured with green light. The relationships are obtained by changing the height of a measurement site and cooling a region near the measurement site.
Figure 9B:
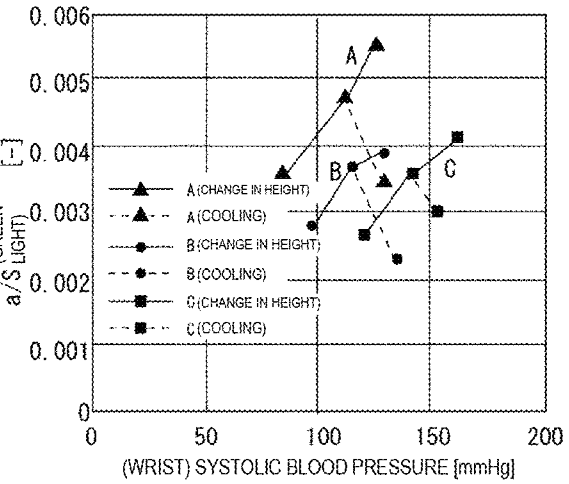
Figure 9C:
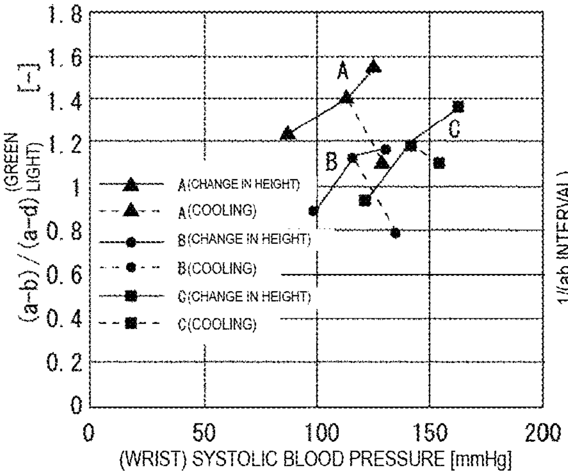
Figure 9D:
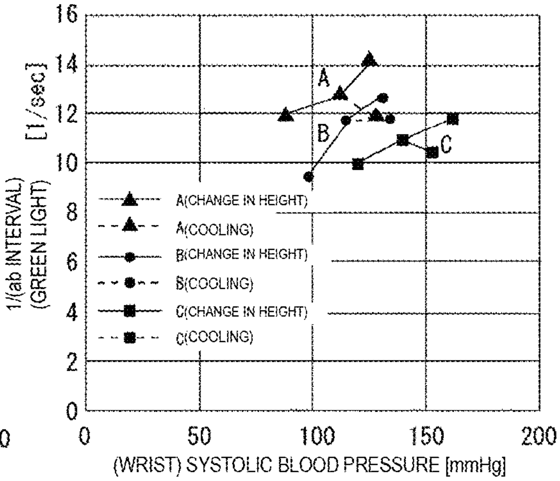
Figure 10A:
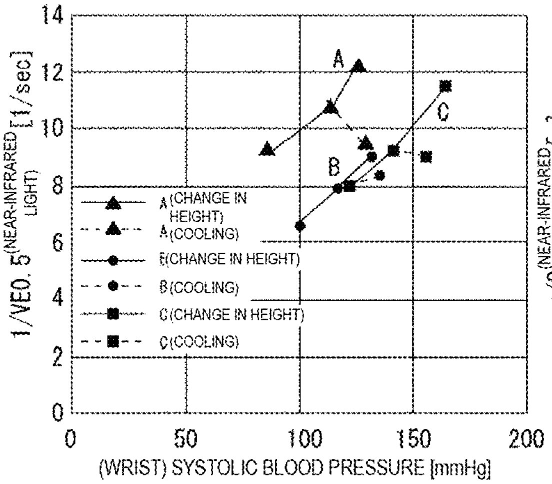
FIGS. 10(*a*) to 10(*d*) illustrate graphs depicting results representing relationships between the systolic blood pressure and plethysmographic-waveform feature values derived from photoplethysmographic signals measured with near-infrared light. The relationships are obtained by changing the height of a measurement site and cooling a region near the measurement site.
Figure 10B:
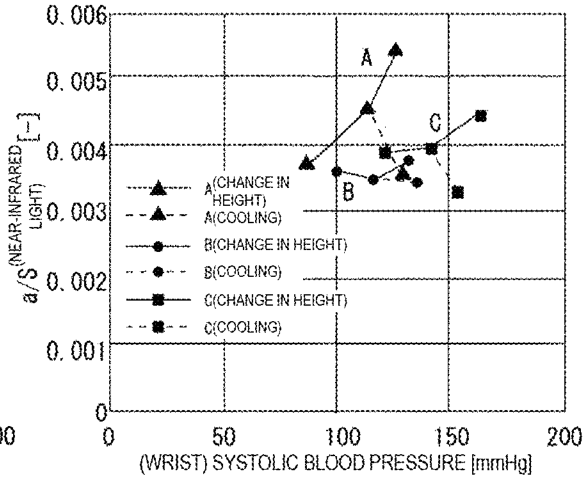
Figure 10C:
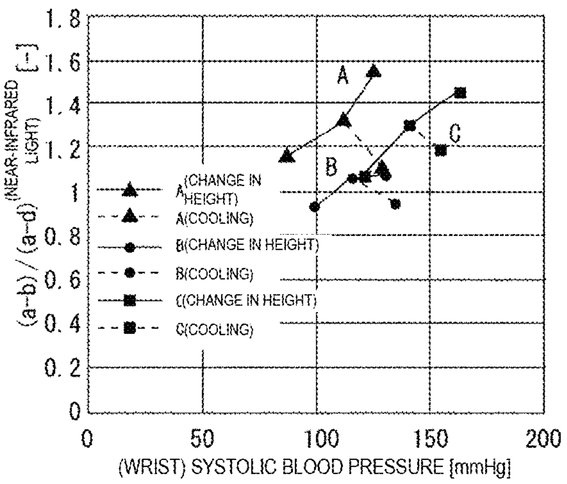
Figure 10D:
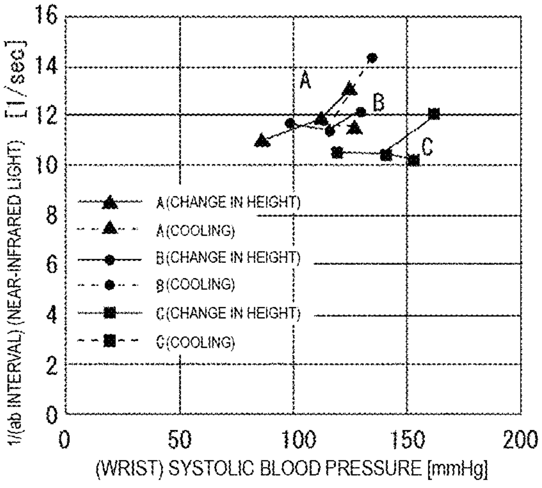

As depicted in FIGS. 8(*a*) to 8 (*c*), these plethysmographic-waveform feature values correlate with the steepness of the rising edge of a waveform of the photoplethysmographic signal 53. Specifically, FIG. 8(*a*) presents a graph depicting two photoplethysmographic signals 53*a* and 53*b* having different steepness of the rising edge of a photoplethysmographic waveform. The horizontal axis on the graph in FIG. 8(*a*) represents time [sec], and the vertical axis on the graph represents the signal intensity of the photoplethysmographic signal 53. It may be seen that, of these two photoplethysmographic signals 53*a* and 53*b*, the photoplethysmographic signal 53*a* represented by a solid line has a steeper rising edge (slope: large) than the photoplethysmographic signal 53*b* represented by a dashed line.

The graph depicted in FIG. 8(*b*) presents dependences of the plethysmographic-waveform feature value 1/VE0.5 and the plethysmographic-waveform feature value a/S on the slope of the photoplethysmographic signals 53*a* and 53*b*. The vertical axis on the graph in FIG. 8(*b*) represents values of the plethysmographic-waveform feature value 1/VE0.5 and the plethysmographic-waveform feature value a/S, and the horizontal axis on the graph is divided into a region for the photoplethysmographic signal 53*b* having a small slope and a region for the photoplethysmographic signal 53*a* having a large slope. The graph in FIG. 8(*b*) indicates that the plethysmographic-waveform feature value 1/VE0.5 and the plethysmographic-waveform feature value a/S are both larger for the photoplethysmographic signal 53*a* having a large slope than for the photoplethysmographic signal 53*b* having a small slope.

The graph depicted in FIG. 8(*c*) presents dependences of the plethysmographic-waveform feature value −a−b)/−a−d) and the plethysmographic-waveform feature value 1/(ab interval) on the slope of the photoplethysmographic signals 53*a* and 53*b*. The vertical axis on the graph in FIG. 8(*c*) represents values of the plethysmographic-waveform feature value −a−b)/−a−d) and the plethysmographic-waveform feature value 1/(ab interval), and the horizontal axis on the graph is divided into a region for the photoplethysmographic signal 53*b* having a small slope and a region for the photoplethysmographic signal 53*a* having a large slope. The graph in FIG. 8(*c*) indicates that the plethysmographic-waveform feature value −a−b)/−a−d) and the plethysmographic-waveform feature value 1/(ab interval) are both larger for the photoplethysmographic signal 53*a* having a large slope than for the photoplethysmographic signal 53*b* having a small slope.

Thus, the figures illustrate that the three plethysmographic-waveform feature values 1/VE0.5, a/S, and (a−b)/(a−d) described above correlate with the steepness of the rising edge of a photoplethysmographic waveform. Namely, the steepness of the rising edge of a photoplethysmographic waveform can be represented by using these plethysmographic-waveform feature values, and these plethysmographic-waveform feature values are expected to have the feature (1) described above. The plethysmographic-waveform feature value 1/(ab interval) is added for comparison as another feature value that correlates with the steepness of the rising edge of a photoplethysmographic waveform.

FIGS. 9(*a*) to 9(*d*) and FIGS. 10(*a*) to 10(*d*) illustrate relationships between the systolic blood pressure and plethysmographic-waveform feature values measured with the measurement method described above; the relationships between the systolic blood pressure and plethysmographic-waveform feature values are obtained by changing the height from the heart to a measurement site (finger); the relationships between the systolic blood pressure and plethysmographic-waveform feature values are also obtained by cooling the region near the elbow of the arm on the same side as the finger, which is kept at chest height as the measurement site. FIGS. 9(*a*), 9(*b*), 9(*c*), and 9(*d*) indicate results for the plethysmographic-waveform feature values 1/VE0.5, a/S, (a−b)/(a−d), and 1/(ab interval), respectively, derived from the photoplethysmographic signal measured with green light emitted from the green LED 211*a*. FIGS. 10(*a*), 10(*b*), 10(*c*), and 10(*d*) indicate results for the plethysmographic-waveform feature values 1/VE0.5, a/S, (a−b)/(a−d), and 1/(ab interval), respectively, derived from the photoplethysmographic signal measured with near-infrared light emitted from the near-infrared LED 211*b*.

The horizontal axis on each graph is the systolic blood pressure [mmHg] measured at a wrist, and the vertical axis is the magnitude of each plethysmographic-waveform feature value. The measurement is performed for three users A, B, and C; the characteristic line A connecting the triangles, the characteristic line B connecting the circles, and the characteristic line C connecting the rectangles represent measurement results for the users A, B, and C, respectively, obtained by changing the height from the heart to the measurement site (finger). A dashed line branching off from each of the characteristic lines represents a measurement result obtained by cooling the region near the elbow of the arm on the same side as the finger, which is kept at chest height as the measurement site.

The characteristic lines A, B, and C indicate that the plethysmographic-waveform feature values depicted in FIGS. 9(*a*), 9(*b*), and 9(*c*), which are derived from the photoplethysmographic signal measured with green light, are nearly proportional to the systolic blood pressure when the height from the heart to the measurement site (finger) is changed. Each of the plethysmographic-waveform feature values decreases as the height from the heart to the measurement site (finger) increases from the stomach, the chest, to the face, and the systolic blood pressure decreases nearly in proportion to each of the plethysmographic-waveform feature values. Based on the dashed lines branching off from the characteristic lines, it is confirmed that the plethysmographic-waveform feature values decrease, and the systolic blood pressure increases as the region near the measurement site is cooled. These results accord with the features (1) and (2) described above, which are expected for the peripheral blood pressure index.

In contrast, the plethysmographic-waveform feature value 1/(ab interval) depicted in FIG. 9(*d*) does not display such a tendency as clearly as the plethysmographic-waveform feature values depicted in FIGS. 9(*a*), 9(*b*), and 9(*c*). In addition, calculated results depicted in FIGS. 10(*a*), 10(*b*), 10(*c*), and 10(*d*) for the plethysmographic-waveform feature values are derived from the photoplethysmographic signals measured with near-infrared light substantially at the same time as with green light, but it may be seen that the calculated results do not display the above tendency as clearly as the results derived from the measurement with green light.

In summary, the plethysmographic-waveform feature values acquired with green light better accord with the features (1) and (2) of the peripheral blood pressure index. This is because living tissue has a high absorbance for green light and green light is mostly absorbed before reaching a region deep in the skin, and thus the plethysmographic-waveform feature values acquired with green light only contain information regarding a shallow region in the skin. Since measured data contains information regarding only a shallow region in the skin, the information contained in the photoplethysmographic signal measured with green light mainly concerns capillaries. Thus, the plethysmographic-waveform feature values depicted in FIGS. 9(*a*), 9(*b*), and 9(*c*) display the features (1) and (2) of the peripheral blood pressure index probably because the plethysmographic-waveform feature values contain a large amount of information regarding capillaries. As described above, to acquire information regarding a shallow region in the skin, an LED or a laser having wavelengths around blue to yellow green (preferably around 500 to 550 nm), which are strongly absorbed by living tissue, is used as a light source in the photoplethysmographic sensor 211, and further the distance between the light source and the photosensitive detector is preferably short, specifically 1 to 3 mm.

The following factors need to be taken care of to accurately acquire the plethysmographic-waveform feature values, which is to be the peripheral blood pressure index.

A first factor is the height from the heart to the measurement site. The peripheral blood pressure index depends on the height from the heart as depicted in FIGS. 9(*a*)-(*d*) and FIGS. 10(*a*)-(*d*). Measurement conditions need to be the same to observe daily variation, weekly variation, or monthly variation. Measurement at heart (chest) height is preferable, but the height may be different from heart height as long as the height from the heart is constant. For example, a position in which the user sits and holds the biological sensor 21 in the hand at chest height, a position in which the user sits and holds the biological sensor 21 in the hand at face height, a position in which the user sits and holds the biological sensor 21 in the hand at stomach height, a position in which the user lies on the back on a flat surface and holds the biological sensor 21 in the hand at chest height, and a position in which the user lies on the back on a flat surface and holds the biological sensor 21 in the hand at the height of the flat surface are postures that everyone may easily take and that an individual may repeatedly take with high reproducibility. For example, further narrowing down “stomach” to “navel” or narrowing down “face” to “forehead” improves the reproducibility of repetition, reducing variation in measurement of a photoplethysmographic signal.

A second factor is a resting condition for the user. The peripheral blood pressure index does not stabilize unless plethysmographic-waveform feature values to be the peripheral blood pressure index are measured in a resting condition. There are mainly two reasons for this. One reason is that a heart rate and a blood pressure do not stabilize for 10 to several tens of seconds or more as a physiological response to bodily movement, and the other reason is that the biological sensor 21 moves relative to the skin. As a former example, a heart rate increases for 10 to several tens of seconds after a small change in sitting posture. It sometimes takes several tens of minutes to return to a resting condition after exercise. The latter is referred to as bodily movement noise, and this noise is unavoidable during intense movement but stops as soon as movement stops. The sensing device 20 is preferably equipped with the acceleration sensor 24 or a gyroscopic sensor to determine that, for example, a resting condition is established if the acceleration remains to be less than a threshold for a fixed period of time, and a photoplethysmographic signal acquired while the resting condition is maintained is preferably used.

A third factor is an excessive pressure applied by the biological sensor 21 to the skin. If the biological sensor 21 applies an excessive pressure to the skin, the accuracy of the peripheral blood pressure index sometimes decreases. It is confirmed that an excessive pressure causes a distortion of the photoplethysmographic waveform in some cases, and a further increase in the pressure obstructs blood flow, resulting in incapability of detecting a photoplethysmographic waveform. Thus, the functionality of detecting an excessive pressure is preferably installed into the sensing device 20. The functionality of detecting an excessive pressure may be achieved with a piezoelectric sensor or a pressure sensor, or an excessive pressure may be detected using a photoplethysmographic waveform. In response to the detection of an excessive pressure, the biological data measurement system 10 preferably provides the user with information such as an instruction not to use the peripheral blood pressure index observed at the time because the peripheral blood pressure index is expected to be inaccurate.

As described above, the peripheral blood pressure index depends on the height at which the sensing device 20 is disposed relative to the heart. Thus, the computer 30 in the biological data measurement system 10 can have the functionality to determine the height from the heart to the sensing device 20 and can calculate the peripheral blood pressure index when the sensing device 20 is at the heart height of a user. In this way, since the height at which the sensing device 20 is disposed relative to the heart is allowed to be restricted, the peripheral blood pressure can be estimated under less influence of the change in the peripheral blood pressure index caused by a difference in the height from the heart.

The computer 30 in the biological data measurement system 10 can have the functionality of estimating the amount of change in the height of the sensing device 20 based on the data from the acceleration sensor 24 in the sensing device 20. The computer 30 can be configured to estimate a peripheral blood pressure based on the peripheral blood pressure index and the amount of change in the height. The change in the height of the sensing device 20 affects the peripheral blood pressure index, and the computer 30 is able to correct for the effect of the change in the height on the peripheral blood pressure index based on the amount of change in the height of the sensing device 20. This correction contributes to improved accuracy of the estimated peripheral blood pressure. In the biological data measurement system 10, the height of the sensing device 20 may be entered from outside via the computer 30.

Figure 11:
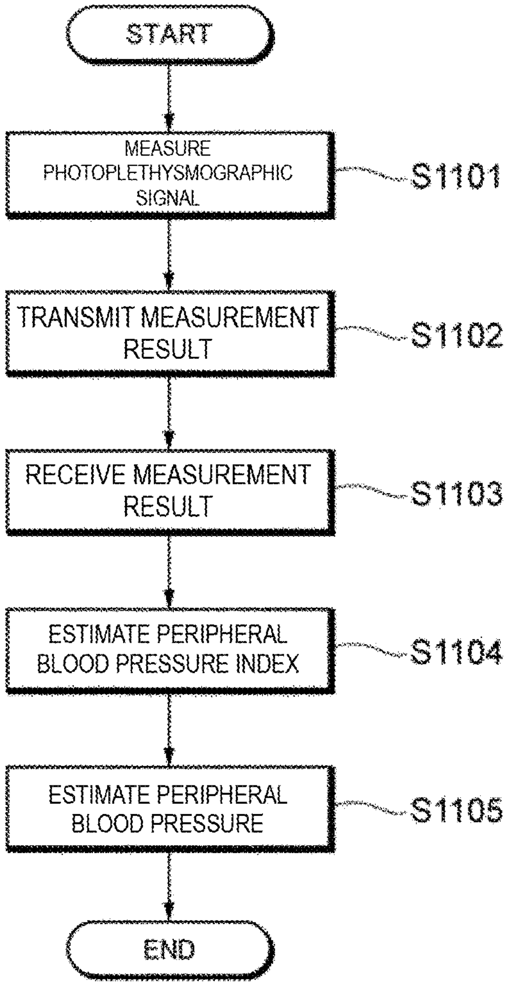
FIG. 11 is a flowchart depicting a process of a method of estimating a peripheral blood pressure in accordance with aspects of the present disclosure.

FIG. 11 is a flowchart depicting an example of a process of the method of estimating a peripheral blood pressure according to an exemplary aspect of the present disclosure. For example, the sensing device 20 and the computer 30 each include an information processing device such as a processor and are configured to execute programs stored in the corresponding non-transitory storage space, and the process by the biological data measurement system 10 is performed by the sensing device 20 and the computer 30 in this way.

In step S1101, the sensing device 20 in the biological data measurement system 10 obtains a photoplethysmographic signal from a finger of a user to which the sensing device 20 is attached. Specifically, the photoplethysmographic sensor 211 measures the photoplethysmographic signal 53 with green light emitted from the green LED 211*a* and measures the photoplethysmographic signal 53 with near-infrared light emitted from the near-infrared LED 211*b*.

In step S1102, the sensing device 20 transmits the measurement result to the computer 30 in the biological data measurement system 10. In step S1103, the computer 30 receives the measurement result obtained by the sensing device 20.

In step S1104, the computer 30 calculates a peripheral blood pressure index of the user. For example, the computer 30 derives the plethysmographic-waveform feature values 1/VE0.5, a/S, and (a−b)/(a−d) from the photoplethysmographic signal 53 measured by the biological sensor 21 and derives a peripheral blood pressure index of the user from the calculated plethysmographic-waveform feature values.

In step S1105, the computer 30 estimates a peripheral blood pressure of the user based on the peripheral blood pressure index stored in a storage such as the memory 322.

An illustrative aspect of the present disclosure has been described as above. The method of estimating a peripheral blood pressure described in the present aspect includes acquiring a photoplethysmographic signal 53 from a capillary or an arteriole at a periphery of a user who is a subject by using a photoplethysmographic sensor 211; calculating a peripheral blood pressure index based on steepness of a rising edge of the photoplethysmographic signal 53, the peripheral blood pressure index serving as an index of a magnitude of a blood pressure in the capillary or the arteriole at the periphery; and estimating the magnitude of the blood pressure in the capillary or the arteriole at the periphery based on the peripheral blood pressure index, and the acquiring and the calculating are performed at the biological data measurement system 10.

According to the present configuration, the photoplethysmographic signal 53 from the capillary or the arteriole at the periphery of the user is acquired by using the photoplethysmographic sensor 211, and the peripheral blood pressure index, which serves as the index of the magnitude of the blood pressure in the capillary or the arteriole at the periphery of the user, is calculated based on the steepness of the rising edge of the acquired photoplethysmographic signal 53. The magnitude of the blood pressure in the capillary or the arteriole at the periphery of the user is estimated based on the calculated peripheral blood pressure index.

In the method of estimating a peripheral blood pressure described above, the steepness of the rising edge of the photoplethysmographic signal 53 is represented by 1/VE0.5, which is the reciprocal of the full width at half maximum of a peak value in the waveform of the velocity plethysmographic signal 51 that is a first derivative of the photoplethysmographic signal 53.

According to the present configuration, the peripheral blood pressure index is calculated based on the plethysmographic-waveform feature value 1/VE0.5 and is less prone to the influence of noise and differences in the photoplethysmographic waveform between individuals, and a peripheral blood pressure can be estimated for various users under less influence of noise and differences between individuals.

In the method of estimating a peripheral blood pressure described above, the steepness of the rising edge of the photoplethysmographic signal 53 is represented by a/S, which is the peak value a of the a wave of the acceleration plethysmographic signal 52 divided by the maximum amplitude S of the photoplethysmographic signal 53, the acceleration plethysmographic signal 52 being a second derivative of the photoplethysmographic signal 53.

According to the present configuration, the peripheral blood pressure index is calculated based on the plethysmographic-waveform feature value a/S. Thus, the peripheral blood pressure index serving as an index of a magnitude of a blood pressure in the capillary or the arteriole at the periphery of the user can be calculated with a simple calculation method.

In the method of estimating a peripheral blood pressure described above, the steepness of the rising edge of the photoplethysmographic signal 53 is represented by a value calculated with the expression (a−b)/(a−d), where a, b, c, and d refer to the peak values of the a wave, the b wave, the c wave, and the d wave, respectively, of the acceleration plethysmographic signal 52 that is a second derivative of the photoplethysmographic signal 53.

According to the present configuration, the peripheral blood pressure index is calculated based on the plethysmographic-waveform feature value (a−b)/(a−d). Thus, also in the present configuration, the peripheral blood pressure index serving as an index of a magnitude of a blood pressure in the capillary or the arteriole at the periphery of the user can be calculated with a simple calculation method.

These plethysmographic-waveform feature values 1/VE0.5, a/S, and (a−b)/(a−d), from which the peripheral blood pressure index is derived, may be used separately, but the peak values a, b, c, and d of the a wave, the b wave, the c wave, and the d wave, respectively, are prone to the effect of bodily movement noise and the pressing state of the photoplethysmographic sensor 211 against a skin and vary widely due to differences between individuals. Accordingly, since 1/VE0.5 may be relatively stably acquired among the plethysmographic-waveform feature values described above, it is preferable that 1/VE0.5 is used alone or 1/VE0.5 is mainly used, and other feature values are used supplementarily. In addition, these plethysmographic-waveform feature values may be weighted and averaged to obtain a weighted average to be used as a feature value, or the magnitudes of these plethysmographic-waveform feature values may be normalized and averaged to obtain a value to be used as a feature value.

In the method of estimating a peripheral blood pressure described above, the photoplethysmographic sensor 211 is configured to cause the light source to emit light having a wavelength range of blue to yellow green.

According to the present configuration, the light source in the photoplethysmographic sensor 211 is configured to emit, to the living tissue of a user, light in the wavelength range of blue to yellow green, which is strongly absorbed by living tissue. Thus, the photoplethysmographic sensor 211 is configured to acquire the photoplethysmographic signal 53 containing a large amount of information regarding a shallow living tissue region close to the skin surface of a body. Accordingly, a blood pressure in a capillary or an arteriole located in a shallow living tissue region of a skin at a periphery can be accurately estimated.

In the method of estimating a peripheral blood pressure described above, in the photoplethysmographic sensor 211, the distance between the light source and the photosensitive element, which is configured to receive light emitted from the light source and reflected, is set to 1 to 3 mm.

According to the present configuration, the distance between the light source and the photosensitive element in the photoplethysmographic sensor 211 is set to a distance that ensures that the light emitted from the light source, scattered or reflected by a capillary or an arteriole at a periphery, and received by the photosensitive element has a sufficient intensity. Accordingly, a blood pressure in the capillary or the arteriole located in a shallow living tissue region of a skin at the periphery can be more accurately estimated.

In the method of estimating a peripheral blood pressure described above, the photoplethysmographic sensor 211 is included in the sensing device 20 to be attached to the finger of a user.

According to the present configuration, the photoplethysmographic signal 53 can be stably acquired continuously or intermittently from the finger of a user with the photoplethysmographic sensor 211 included in the sensing device 20. Accordingly, a blood pressure in the capillary or the arteriole at the periphery of the user can be stably estimated.

The method of estimating a peripheral blood pressure described above can further include detecting a pressing state of the photoplethysmographic sensor 211 against a measurement site of the user. In this case, the sensing device 20 includes a pressing-state detecting sensor formed by a device such as a piezoelectric element and configured to detect a pressing state of the photoplethysmographic sensor 211 against a measurement site of the subject. The signal processing device 32 is configured to determine the validity of the estimated peripheral blood pressure index based on the detected pressing state.

The photoplethysmographic sensor 211 needs to be in close contact with the skin at a measurement site of the user to stably measure the photoplethysmographic signal 53, but an excessive pressure applied to the measurement site of the user by the photoplethysmographic sensor 211 obstructs blood flow, resulting in a decrease in the accuracy of estimating a peripheral blood pressure. However, since the present configuration further includes detecting a pressing state of the photoplethysmographic sensor 211 against the measurement site of the user by using the pressing-state detecting sensor, a state in which the photoplethysmographic sensor 211 applies an excessive pressure to the measurement site of the user is detected, leading to an appropriate procedure, such as using no peripheral blood pressure estimated at the time.

Accordingly, the exemplary aspects of the present disclosure provide a method of estimating a peripheral blood pressure by which the magnitude of a blood pressure in a capillary or an arteriole at a periphery may be estimated in a simple and non-invasive manner without causing a burden on the user.

In general, the description of the aspects disclosed should be considered as being illustrative in all respects and not being restrictive. The scope of the present disclosure is shown by the claims rather than by the above description, and is intended to include meanings equivalent to the claims and all changes in the scope. While preferred aspects of the invention have been described above, it is to be understood that variations and modifications will be apparent to those skilled in the art without departing from the scope and spirit of the invention.

DESCRIPTION OF REFERENCE SYMBOLS

10 biological data measurement system
20 sensing device
21 biological sensor
211 photoplethysmographic sensor
211*a* green LED (light emitting element)
211*b* near-infrared LED (light emitting element)
211*c* photosensitive element
22 control circuit
23 communication module

24 acceleration sensor
25 casing
30 computer
31 communication module
32 signal processing device

The invention claimed is:

1. A method of estimating a peripheral blood pressure, the method comprising:

acquiring a photoplethysmographic signal from a capillary or an arteriole at a periphery of a subject via a photoplethysmographic sensor;

upon receipt of the photoplethysmographic signal of a single cardiac cycle, calculating a peripheral blood pressure index of the single cardiac cycle based on a steepness of a rising edge of the photoplethysmographic signal, the peripheral blood pressure index indicating an index of a magnitude of a blood pressure in the capillary or the arteriole at the periphery; and upon calculation of the peripheral blood pressure index of the single cardiac cycle, estimating the magnitude of the blood pressure in the capillary or the arteriole at the periphery based on the peripheral blood pressure index, wherein the acquiring and the calculating are performed via a biological data measurement system, wherein the steepness further includes information regarding a difference in peak value (a−b) and a difference in peak value (a−d), where a, b, and d represent peak values of an a wave, a b wave, and a d wave, respectively, of an acceleration plethysmographic signal that is a second derivative of the photoplethysmographic signal, wherein the steepness increases as a magnitude of the peak difference (a−b) relative to the peak difference (a−d) increases, and wherein the acceleration plethysmographic signal has been subjected to a normalization process such that a maximum of the acceleration plethysmographic signal becomes 1.

2. The method of estimating the peripheral blood pressure according to claim 1, wherein the steepness further includes information regarding the peak value of the wave of the acceleration plethysmographic signal and a maximum amplitude of the photoplethysmographic signal, the acceleration plethysmographic signal being the second derivative of the photoplethysmographic signal.

3. The method of estimating the peripheral blood pressure according to claim 1, wherein the photoplethysmographic sensor includes a light source configured to emit light in a wavelength range of blue to yellow green.

4. The method of estimating the peripheral blood pressure according to claim 3, wherein a distance between the light source and a photosensitive element is set to 1 to 3 mm in the photoplethysmographic sensor, and wherein the photosensitive element receives light emitted from the light source and reflected.

5. The method of estimating the peripheral blood pressure according to claim 1, wherein the photoplethysmographic sensor is included in a device configured to be attached to a finger of the subject.

6. The method of estimating the peripheral blood pressure according to claim 1, further comprising detecting a pressing state of the photoplethysmographic sensor against a measurement site of the subject.

7. A biological data measurement system comprising:

a sensing device including a photoplethysmographic sensor configured to acquire a photoplethysmographic signal from a capillary or an arteriole at a periphery of a subject; and a signal processing device configured to:

calculate, upon receipt of the photoplethysmographic signal of a single cardiac cycle, a peripheral blood pressure index of the single cardiac cycle based on steepness of a rising edge of the photoplethysmographic signal, and estimate, upon calculation of the peripheral blood pressure index of the single cardiac cycle, a magnitude of a blood pressure in the capillary or the arteriole at the periphery, wherein the steepness increases based on a width of a first peak during a single cardiac cycle in a waveform of a velocity plethysmographic signal that is a first derivative of the photoplethysmographic signal width decreases, and wherein the velocity plethysmographic signal has been subjected to a normalization process such that a maximum of the velocity plethysmographic signal becomes 1.

8. The biological data measurement system according to claim 7, wherein the steepness further includes information regarding a peak value of a wave of an acceleration plethysmographic signal and a maximum amplitude of the photoplethysmographic signal, wherein the acceleration plethysmographic signal being a second derivative of the photoplethysmographic signal.

9. The biological data measurement system according to claim 7, wherein the steepness further includes information regarding a difference in peak value (a−b) and a difference in peak value (a−d), where a, b, and d represent peak values of an a wave, a b wave, and a d wave, respectively, of an acceleration plethysmographic signal that is a second derivative of the photoplethysmographic signal.

10. The biological data measurement system according to claim 7, wherein the photoplethysmographic sensor includes a light source configured to emit light in a wavelength range of blue to yellow green.

11. The biological data measurement system according to claim 10, wherein a distance between the light source and a photosensitive element is set to 1 to 3 mm in the photoplethysmographic sensor, and wherein the photosensitive element being configured to receive light emitted from the light source and reflected.

12. The biological data measurement system according to claim 7, wherein the photoplethysmographic sensor is included in a device to be attached to a finger of the subject.

13. The biological data measurement system according to claim 7, wherein the sensing device includes a pressing-state detecting sensor configured to detect a pressing state of the photoplethysmographic sensor against a measurement site of the subject, and the signal processing device is configured to determine validity of the peripheral blood pressure index based on the pressing state.

14. A method of estimating a peripheral blood pressure comprising:

acquiring a signal from a user via a photoplethysmographic sensor;

upon receipt of the photoplethysmographic signal of a single cardiac cycle, calculating a peripheral blood pressure index of the single cardiac cycle based on a steepness of a rising edge of the signal, the peripheral blood pressure index indicating an index of a magnitude of a blood pressure in a capillary or an arteriole at a periphery of the user; and upon calculation of the peripheral blood pressure index of the single cardiac cycle, estimating the magnitude of the blood pressure in the capillary or the arteriole at the periphery based on the peripheral blood pressure index, wherein the steepness includes information regarding a width of a first peak during the single cardiac cycle in a waveform of a velocity plethysmographic signal that is a first derivative of the photoplethysmographic signal, and wherein the velocity plethysmographic signal has been subjected to a normalization process such that a maximum of the velocity plethysmographic signal becomes 1.

15. The method of estimating the peripheral blood pressure according to claim 14, wherein the acquiring and the calculating are performed via a biological data measurement system.

16. The method of estimating the peripheral blood pressure according to claim 14, wherein the signal is a photoplethysmographic signal from the capillary or the arteriole at the periphery of the user.

17. The method of estimating the peripheral blood pressure according to claim 14, wherein:

the photoplethysmographic sensor includes a light source configured to emit light in a wavelength range of blue to yellow green;

a distance between the light source and a photosensitive element is set to 1 to 3 mm in the photoplethysmographic sensor, and the photosensitive element receives light emitted from the light source and reflected.

* * * * *